(12) United States Patent
Yonemitsu et al.

(10) Patent No.: US 11,723,924 B2
(45) Date of Patent: Aug. 15, 2023

(54) HIGHLY ACTIVE NK CELL AND USE THEREOF

(71) Applicants: Yoshikazu Yonemitsu, Fukuoka (JP); GAIA BioMedicine Inc., Fukuoka (JP)

(72) Inventors: Yoshikazu Yonemitsu, Fukuoka (JP); Yui Harada, Fukuoka (JP); Koji Teraishi, Fukuoka (JP)

(73) Assignees: Yoshikazu Yonemitsu, Fukuoka (JP); GAIA BioMedicine Inc., Tokyo (JP)

( * ) Notice: Subject to any disclaimer, the term of this patent is extended or adjusted under 35 U.S.C. 154(b) by 669 days.

(21) Appl. No.: 16/612,091

(22) PCT Filed: May 11, 2018

(86) PCT No.: PCT/JP2018/018236
§ 371 (c)(1),
(2) Date: Nov. 8, 2019

(87) PCT Pub. No.: WO2018/207900
PCT Pub. Date: Nov. 15, 2018

(65) Prior Publication Data
US 2021/0330707 A1    Oct. 28, 2021

(30) Foreign Application Priority Data

May 12, 2017 (JP) ................................ 2017-095288

(51) Int. Cl.
*A61K 35/17* (2015.01)
*C12N 5/0783* (2010.01)
*A61K 45/06* (2006.01)

(52) U.S. Cl.
CPC .............. *A61K 35/17* (2013.01); *A61K 45/06* (2013.01); *C12N 5/0646* (2013.01); *C12N 2500/90* (2013.01); *C12N 2501/2302* (2013.01)

(58) Field of Classification Search
CPC ....... A61K 35/17; A61K 39/00; C12N 5/0646
See application file for complete search history.

(56) References Cited

U.S. PATENT DOCUMENTS

| 9,090,876 B2 | 7/2015 | Velardi et al. |
| 2005/0037002 A1 | 2/2005 | Velardi et al. |
| 2009/0123442 A1 | 5/2009 | Dilber et al. |
| 2014/0080148 A1 | 3/2014 | Spanholtz |
| 2014/0120072 A1 | 5/2014 | Yonemitsu et al. |
| 2015/0010583 A1 | 1/2015 | Spanholtz |

FOREIGN PATENT DOCUMENTS

| CN | 103620022 A | 3/2014 |
| CN | 104645327 A | 5/2015 |
| JP | 2006-528627 A | 12/2006 |
| JP | 4748491 B1 | 8/2011 |
| JP | 2013-27385 A | 2/2013 |
| JP | 5572863 B2 | 8/2014 |
| JP | 2016-513460 A | 5/2016 |
| KR | 10-2012-0090485 A | 8/2012 |
| WO | 2005/009466 A1 | 2/2005 |
| WO | 2012/176796 A1 | 12/2012 |
| WO | 2014-165177 A1 | 10/2014 |
| WO | 2015/154012 A1 | 10/2015 |
| WO | 2016/210241 A1 | 12/2016 |
| WO | 2017/042393 A1 | 3/2017 |

OTHER PUBLICATIONS

Lorenzo, M., "Dissecting CD56dim human NK cells", BLOOD, (2010), vol. 116, No. 19, pp. 3689-3691, (3 pages).
Arima, Y., "The role of Killer Cell Immunoglobulin-like receptors in cure by Hematopoietic Stem Cell Transplantation", Journal of Hematopoietic Cell Transplantation, (2014), vol. 3, No. 1, pp. 12-26, with English abstract, (15 pages).
International Search Report and Written Opinion dated Aug. 14, 2018, issued in counterpart application No. PCT/JP2018/018236, with English translation. (13 pages).
Notification of Transmittal of Translation of the International Preliminary Report on Patentability (Form PCT/IB/338) issued in counterpart International application No. PCT/JP2018/018236 dated Nov. 21, 2019 with Forms PCT/IB/326, PCT/IB/373 and PCT/ISA/237, with English translation. (17 pages).
Takahashi, E., et al., "Induction of CD16+ CD56bright NK Cells with Antitumour Cytotoxicity not only from CD16-CD56bright NK Cells but also from CD16– CD56dim NK Cells" Scandinavian Journal of Immunology, (2007), vol. 65, pp. 126-138, cited in ISR and Written Opinion dated Aug. 14, 2018, IPRP dated Nov. 21, 2019 and JP Office Actions dated Aug. 14, 2018, Feb. 19, 2019, and Jul. 9, 2019. (13 pages).
Wang, W., et al., "NK cell-mediated antibody-dependent cellular cytotoxicity in cancer immunotherapy", Frontiers in Immunology, (2015), vol. 6, article 368, pp. 1-15, cited in ISR and Written Opinion dated Aug. 14, 2018, IPRP dated Nov. 21, 2019 and JP Office Actions dated Feb. 19, 2019 and Jul. 9, 2019. (15 pages).
Beziat, V., et al., "CD56bright CD16+ NK Cells: a Functional Intermediate Stage of NK Cell Differentiation", The Journal of Immunology, (2011), vol. 186, pp. 6753-6761, cited in ISR and Written Opinion dated Aug. 14, 2018. (9 pages).
Poli, A., et al., "CD56bright natural killer (NK) cells: an important NK cell subset", Immunology, 2009, vol. 126, pp. 458-465, cited in ISR and Written Opinion dated Aug. 14, 2018 and JP Office Action dated Aug. 14, 2018. (8 pages).
Michel, T., et al., "Human CD56bright NK cells: an Update", The Journal of Immunology, (2016), vol. 196, pp.2923-2931, cited in ISR and Written Opinion dated Aug. 14, 2018 and JP Office Action dated Aug. 14, 2018. (9 pages).

(Continued)

*Primary Examiner* — Daniel C Gamett
(74) *Attorney, Agent, or Firm* — WHDA, LLP

(57) ABSTRACT

An NK cell showing higher cytotoxic activity is provided. An object of the present invention is to provide a pharmaceutical composition for NK cell therapies expected to be highly effective. The present invention provides an NK cell having the following characteristics of (1) and (2) or a population thereof. (1) the NK cell is CD16-positive, highly expresses CD56, and is CD57-negative, and (2) the NK cell is NKG2C-positive, is NKG2A-negative or lowly expresses NKG2A, and is CD94-positive. The present invention also provides a pharmaceutical composition containing a population of such NK cells, and a therapeutically effective amount of antibodies.

12 Claims, 9 Drawing Sheets

(56) References Cited

OTHER PUBLICATIONS

Office Action dated Aug. 14, 2018, issued in counterpart JP application No. 2017-095288, with English translation. (11 pages).
Office Action dated Feb. 19, 2019, issued in counterpart JP application No. 2017-095288, with English translation. (12 pages).
Office Action dated Aug. 20, 2019, issued in counterpart JP application No. 2017-095288, with English translation. (8 pages).
Lopez-Verges, S., et al., "CD57 defines a functionally distinct population of mature NK cells in the human CD56dim CD16+ NK-cell subset", BLOOD, (2010), vol. 116, No. 19, pp. 3865-3874. (11 pages).
Office Action dated Jul. 9, 2019, issued in counterpart JP application No. 2019-094305, with English translation. (12 pages).
Fujiwara, Blood Medicine, (2017), vol. 74, No. 1, p. 51-57, cited in JP Office Action dated Jul. 9, 2019. (9 pages).
Ito, Bio Clinica, (2015), vol. 30, No. 3, p. 243-247, cited in JP Office Action dated Jul. 9, 2019. (7 pages).
Yamano, Y., et al., "Humanized anti CCR4 antibody KW0761 targets HTLV-1 infected CD4+ CCR4+ and CD8+CCR4+ T cells to treat HAM/TSP", Retrovirorogy, (2015), vol. 12 Suppl 1, No. 023, p. 1, cited in JP Office Action dated Jul. 9, 2019. (1 page).
Katano, I., et al., "Predominant Development of Mature and Functional Human NK Cells in a Novel Human IL-2-Producing Transgenic NOG Mouse", The Journal of Immunology, (2015), vol. 194, pp. 3513-3525, cited in JP Office Action dated Jul. 9, 2019. (14 pages).
Office Action dated Apr. 22, 2022, issued in counterpart TW application No. 107115901, with English translation. (8 pages).
Office Action dated Jun. 29, 2021, issued in counterpart JP application No. 2020-067164, with English translation. (10 pages).
Shin-ichi NIHIRA, "Development of HER2-specific humanized antibody Herceptin", Journal of Pharmaceutical Affairs, 2003, vol. 122, p. 504-514, cited in JP Office Action dated Jun. 29, 2021. (12 pages).
Kaori Fujimoto-Ouchi, "Current status and prospects of antibody drugs-trastuzmab", Journal of Pharmaceutical Affairs, 2010, vol. 136, p. 210-214, cited in JP Office Action dated Jun. 29, 2021. (6 pages).
Decision of Dismissal of Amendment dated Jan. 11, 2022, issued in counterpart JP application No. 2020-067164, with English translation. (5 pages).
Office Action dated Dec. 8, 2020, issued in counterpart to JP Application No. 2020-067154, with English translation (10 pages).
Extended Search Report dated Feb. 3, 2021, issued in counterpart EP Application No. 18797854.9 (10 pages).
Lehmann, Dorit et al., "Ex Vivo Generated Natural Killer Cells Acquire Typical Natural Killer Receptors and Display a Cytotoxic Gene Expression Profile Similar to Peripheral Blood Natural Killer Cells", Stem Cells and Development, vol. 21, No. 16, Jan. 1, 2012, pp. 2926-2938; Cited in EESR dated Feb. 3, 2021.
Childs, Richard W. et al., "Therapeutic approaches to enhance natural killer cell cytotoxicity against cancer: the force awakens", Nature Reviews, vol. 14, No. 7, May 2015, pp. 487-498; Cited in EESR dated Feb. 3, 2021.
Office Action dated Jul. 7, 2020, issued in counterpart JP Application No. 2020-067164, with English translation (6 pages).
Voshol, Hans et al., "Human natural killer cells: a convenient purification procedure and the influence of cryopreservation on cytotoxic activity", Journal of Immunological Methods, 1993, vol. 165, No. 1, pp. 21-30.
Office Action dated Oct. 25, 2022, issued in the corresponding Chinese patent Application No. 201880030429.1 with its English Machine Translation. (17 pages).
Office Action dated Oct. 28, 2022, issued in the corresponding Taiwanese patent application No. 107115901 with its English Translation. (10 pages).
Wang, Database of whole text of dissertations for doctor's degree, Medical sections, vol. 10, pp. E059-E021; with English Translation; Cited in CN Office Action dated Oct. 25, 2022, (101 pages).
Office Action dated May 9, 2023, issued in counterpart CN application No. 201880030429.1, with partial English translation. (13 pages).
Liao Zijun et al., "Modern Lymphoma Oncology," Shaanxi Science and Technology Press, Jun. 30, 2013, p. 754, with partial English translation. (7 pages).
Office Action dated Jun. 6, 2023, issued in counterpart EP application No. 18797854.9. (4 pages).

[Fig. 1]
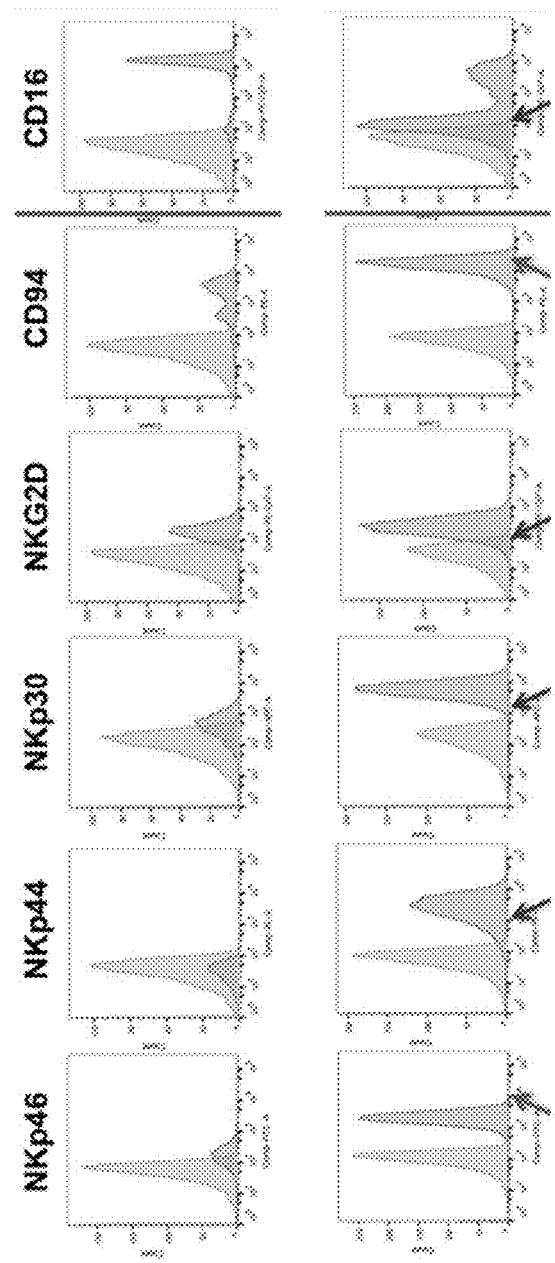

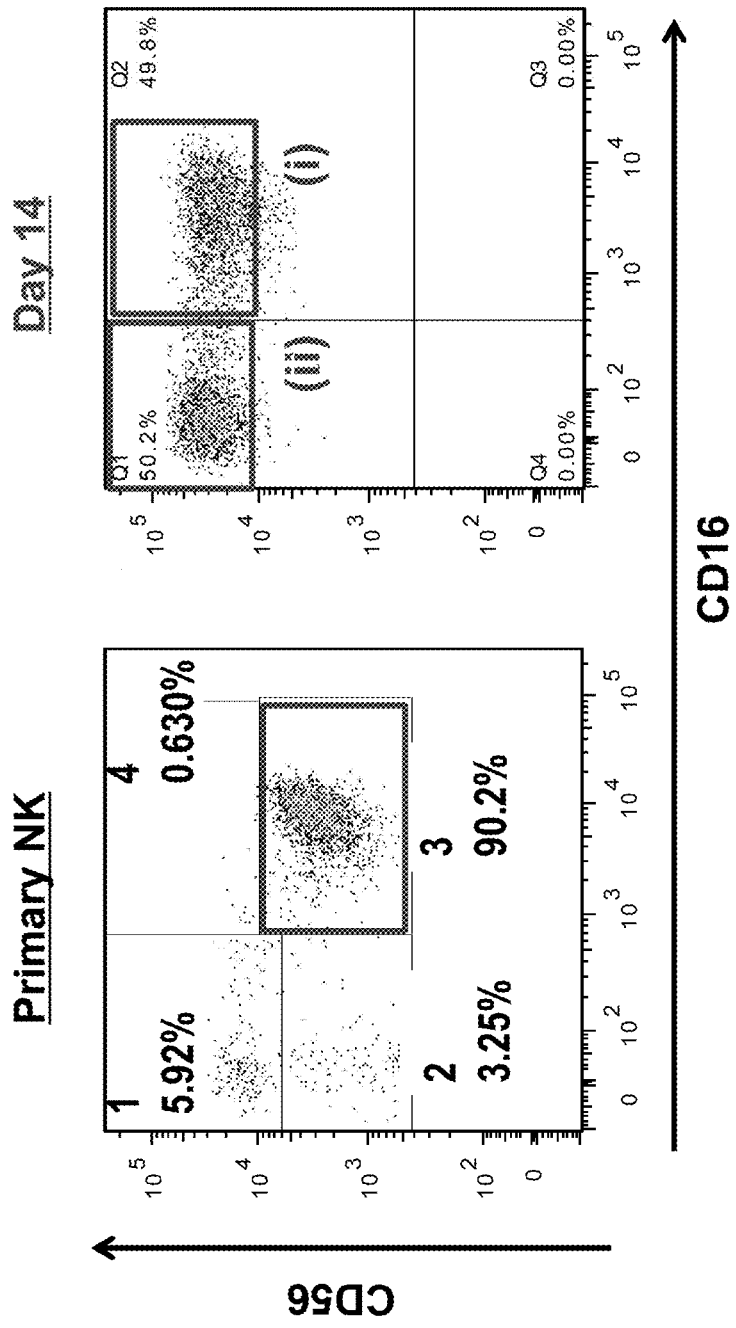
[Fig. 2A]

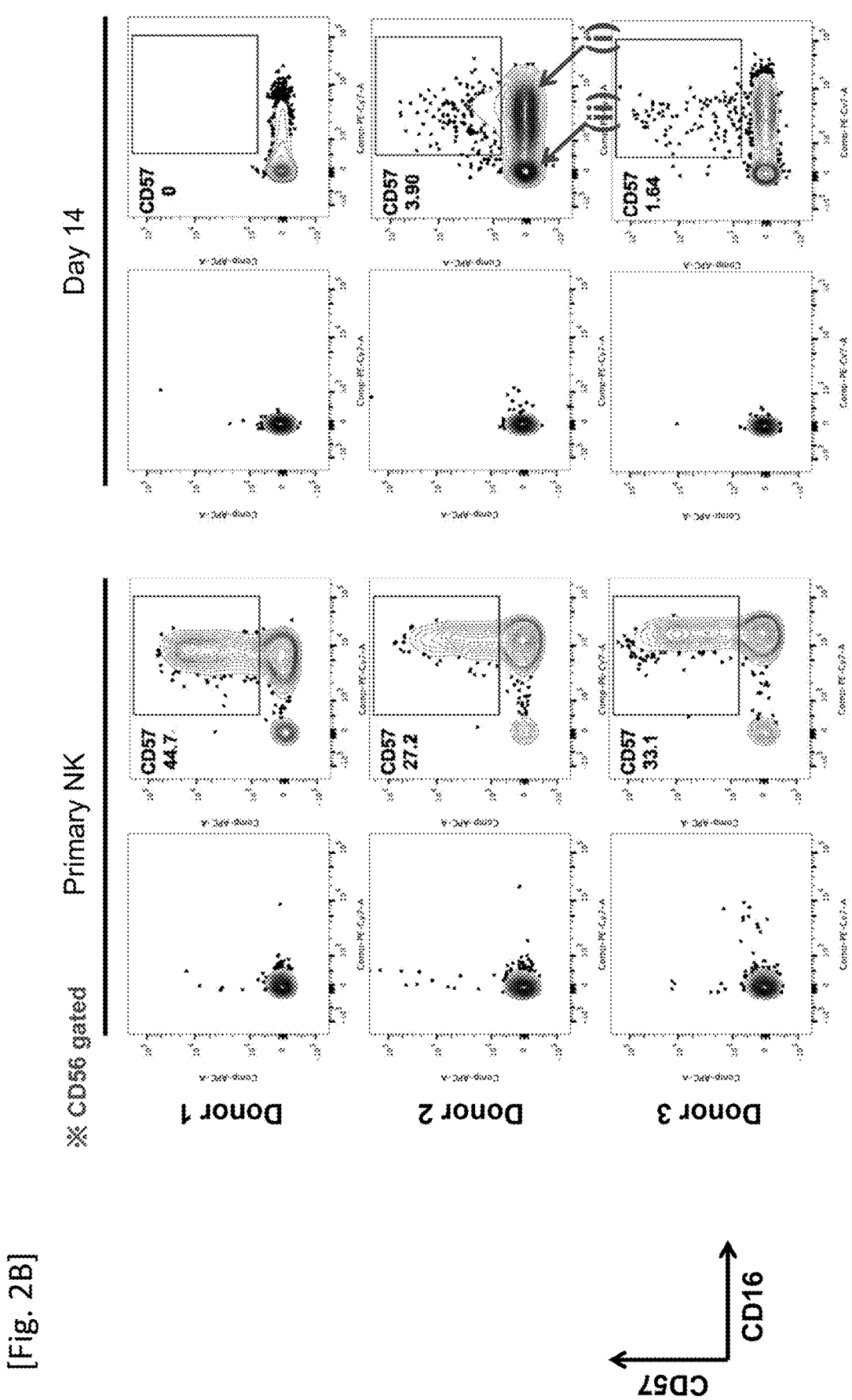
[Fig. 2B]

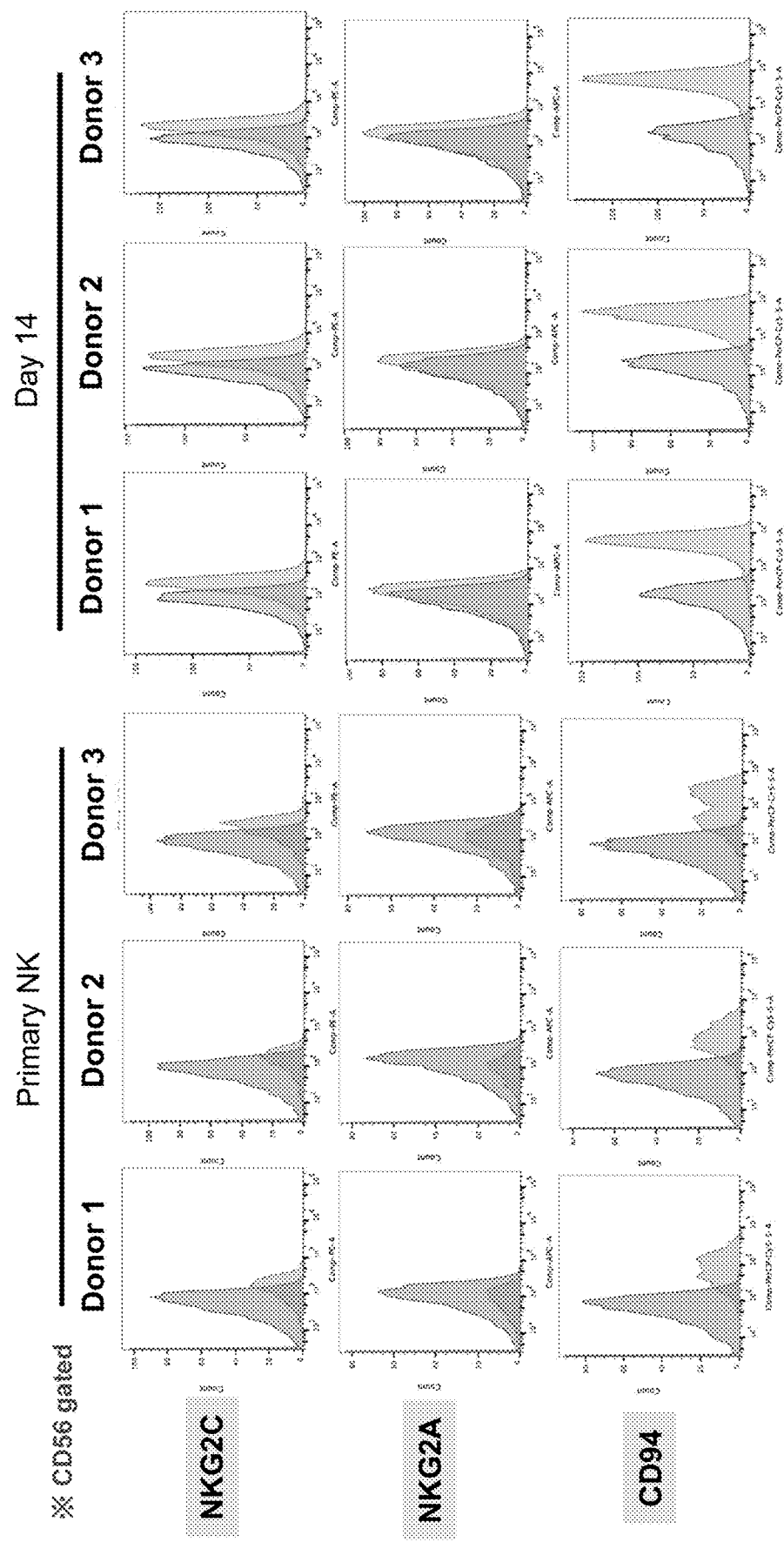

[Fig. 3]
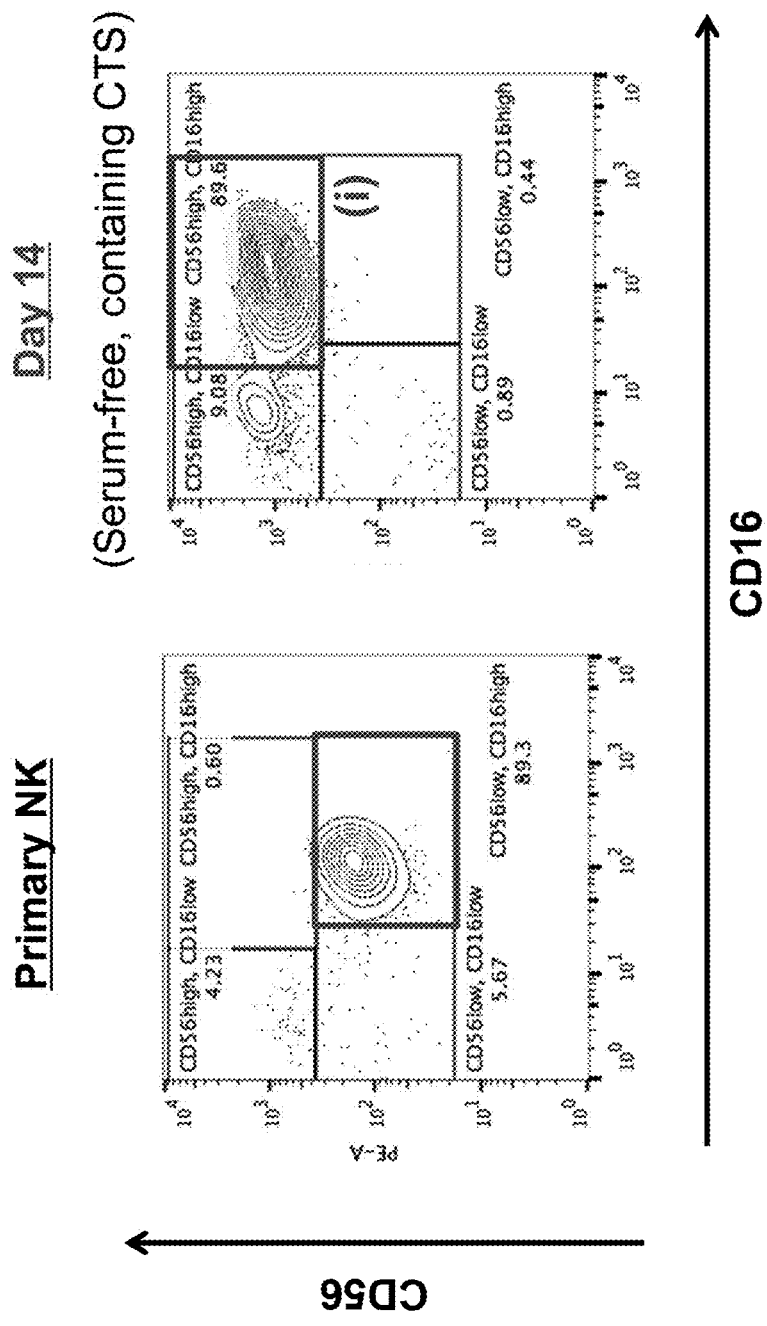

[Fig. 4]
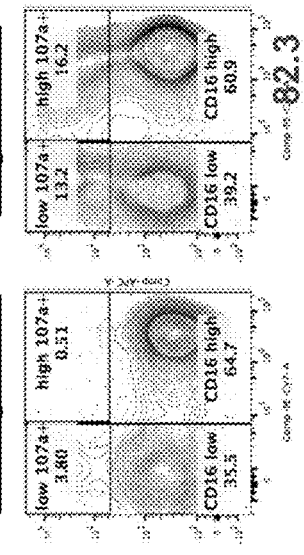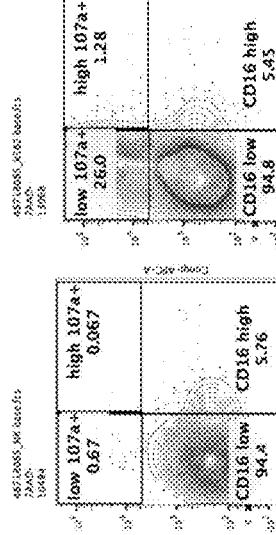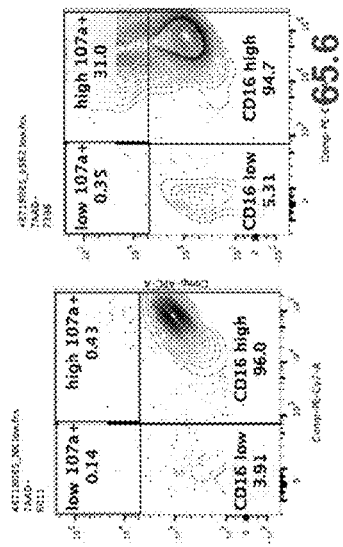

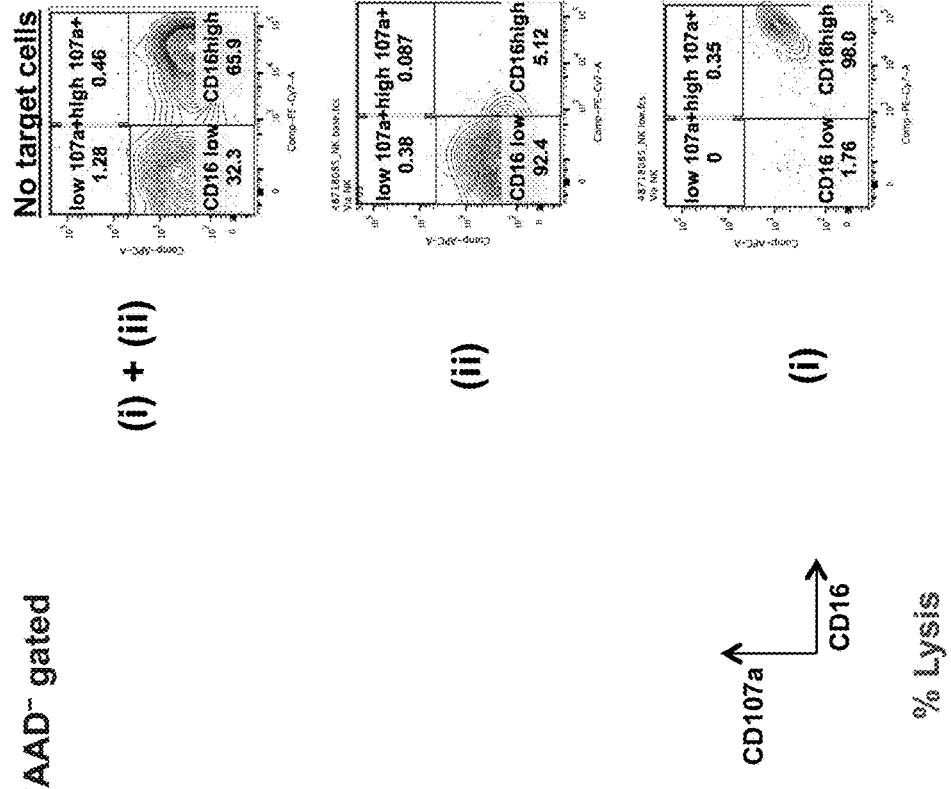
[Fig. 5]

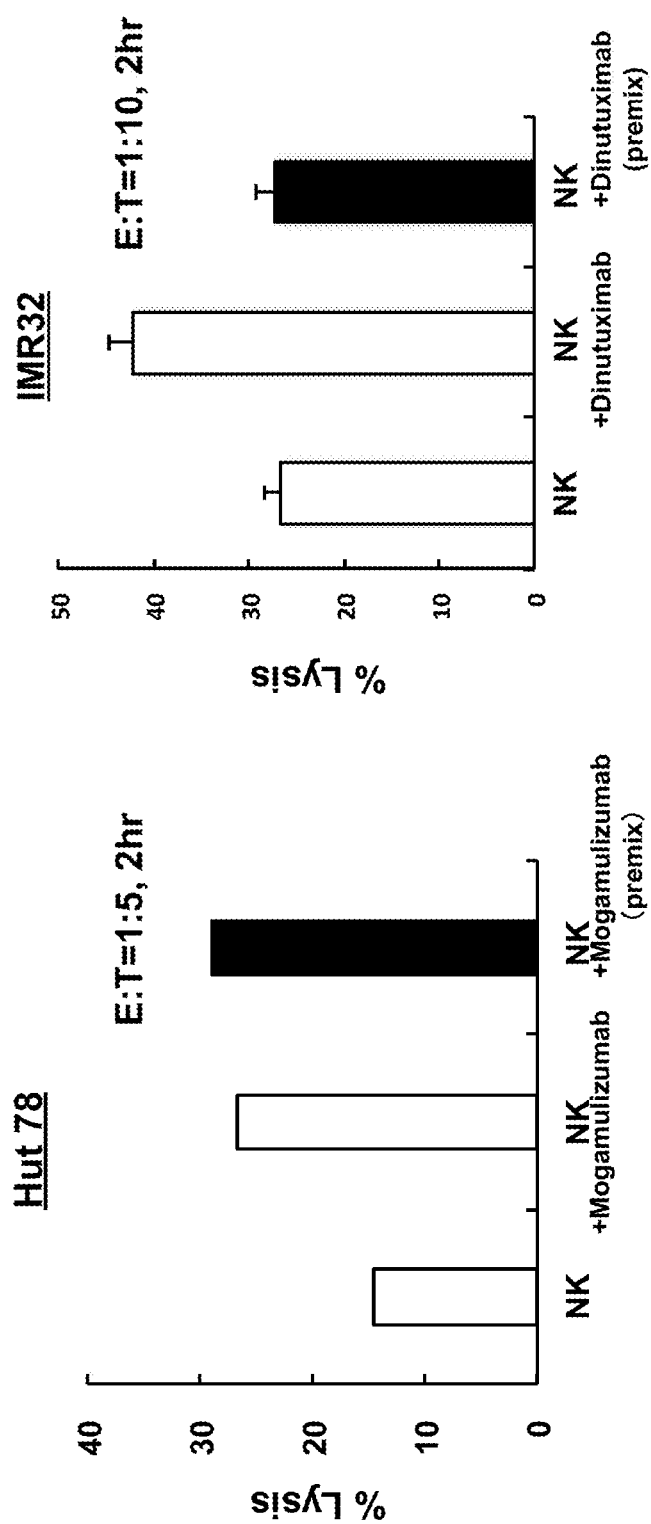
[Fig. 6]

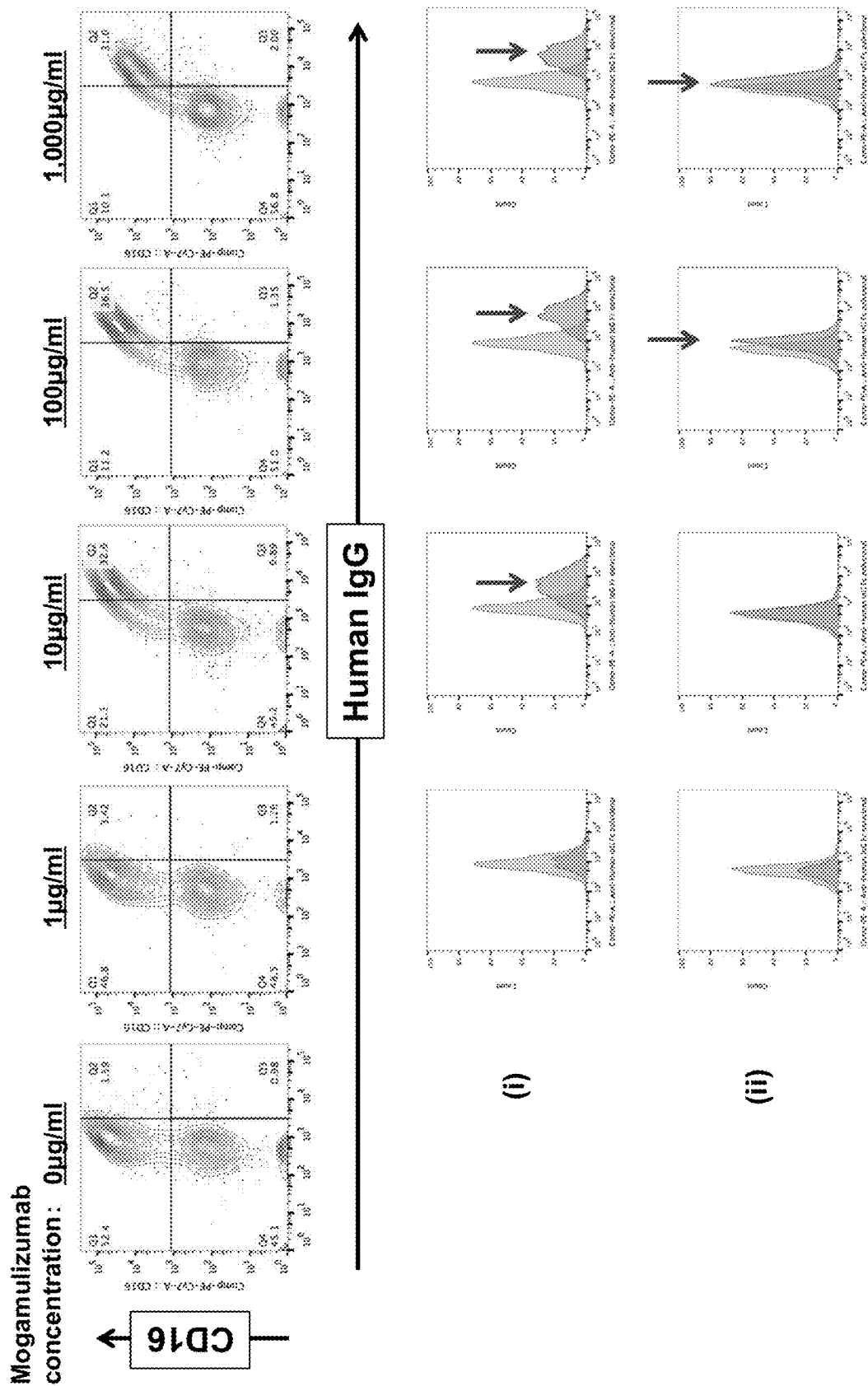

HIGHLY ACTIVE NK CELL AND USE THEREOF

TECHNICAL FIELD

The present invention relates to a natural killer cell (NK cell) showing a high cytotoxic activity, and use thereof.

BACKGROUND ART

Natural killer cells (NK cells) are cytotoxic lymphocytes that work as a main factor of the innate immunity. It is known that human peripheral blood NK cells are CD16-positive, express CD56 at a low level, and are CD57-positive (Non-patent documents 1 and 2).

As one of the mechanisms of the cytotoxicity of NK cells, antibody-dependent cellular cytotoxicity (ADCC) is known. NK cells have Fc receptors (CD16) on the cell surfaces thereof, and ADCC is a mechanism that NK cells bind to antibodies binding with target cells via the Fc receptors to injure the target cells.

NK cells are important for rejection of tumor cells or virus-infected cells. NK cell therapies in which NK cells extracted from patients themselves are increased and activated several hundreds to several thousands of times by cultivation in the outside of the patients, and returned to the patients attract attention as therapies that give comparatively few side reactions. About $1 \times 10^{10}$ of monocytes can usually be collected by one time of apheresis of peripheral blood of normal adult, and $7 \times 10^8$ of NK cells will be obtained from them if the percentage of NK cells constituting peripheral blood monocytes is supposed to be about 7%. On the other hand, if body weight of a patient is supposed to be 60 kg, it is considered that $6 \times 10^6$ to $4.8 \times 10^9$ of NK cells are required. Therefore, techniques for culturing NK cells obtained from a donor to proliferate them, and thereby obtain NK cells in an amount sufficient for annihilating target cells are being developed. For example, Patent document 1 proposes a method for proliferating NK cells, which comprises the step of preparing a cell population containing NK cells, the step of eliminating T cells from the cell population containing NK cells, and the step of culturing the cells remained after the elimination of T cells in a medium containing 2500 to 2813 IU/mL of IL-2 as a sole cytokine without using feeder cells.

PRIOR ART REFERENCES

Patent Document

Patent document 1: Japanese Patent Unexamined Publication (KOKAI) No. 2013-27385 (Japanese Patent No. 5572863)

Non-Patent Documents

Non-patent document 1: Lorenzo, M., Blood, 116:3689 (2010)
Non-patent document 2: Arima Y, Journal of Hematopoietic Cell Transplantation, Vol. 3, No. 1, 12 (2014)

DISCLOSURE OF THE INVENTION

Object to be Achieved by the Invention

According to the investigations of the inventors of the present invention, although primary NK cells obtained from peripheral blood highly express CD16, if NK cells are used as effecter cells (E), and co-cultured with the K562 cells as the target cells (T) at a mixing ratio (E:T) of 1:1, the cytotoxic activity thereof is about 10 to 20%. Therefore, NK cells that show higher cytotoxic activity are desirable.

One of action mechanisms of many antibody drugs is based on the ADCC activity of NK cells. In order that NK cells should exhibit the ADCC activity, it is necessary that CD16 on the NK cell surfaces should bind with antibodies that can induce antibody-dependent cellular cytotoxicity. However, there has been no report about effective combination of an antibody drug and NK cell therapy so far.

Means for Achieving the Object

The present invention provides the followings.
[1] An NK cell having the following characteristics (1) and (2) or a population thereof:
(1) the NK cell is CD16-positive, highly expresses CD56, and is CD57-negative.
(2) the NK cell is NKG2C-positive, is NKG2A-negative or lowly expresses NKG2A, and is CD94-positive.
[2] The population according to 1, which contains a population of NK cells that highly express CD16, and a population of NK cells that lowly express CD16.
[3] The NK cell or a population thereof according to 1, wherein the NK cell highly expresses CD16.
[4] The NK cell or a population thereof according to 1, wherein the NK cell lowly expresses CD16.
[5] The NK cell or a population thereof according to any one of 1 to 4, wherein the NK cell further has the following characteristic (3):
(3) when the NK cell is used as effecter cells (E), and co-cultured with K562 cells as target cells (T) at a mixing ratio (E:T) of 1:1, the NK cells show a cytotoxicity of 50% or higher.
[6] A method for preparing the NK cell or a population thereof according to any one of 1 to 5, which comprises the following step:
the step of culturing a population of primary NK cells in a medium containing IL-2 or a serum-free medium.
[7] The preparation method according to 6, wherein the population of primary NK cells has undergone the step of removing CD3-positive cells.
[8] A pharmaceutical composition containing the population of NK cells according to any one of 1 to 5, and an additive acceptable for a drug.
[9] A pharmaceutical composition containing a population of NK cells, and a therapeutically effective amount of antibodies.
[10] The pharmaceutical composition according to 9, wherein the population of NK cells is the population of NK cells according to any one of 1 to 5.
[11] The pharmaceutical composition according to 9 or 10, wherein the antibodies can induce antibody-dependent cellular cytotoxicity (ADCC).
[12] The pharmaceutical composition according to any one of 9 to 11, wherein at least a part of the antibodies bind with the NK cells.

BRIEF DESCRIPTION OF THE DRAWINGS

FIG. 1 Expressions of major cell surface markers on the NK cells on day 14 of the culture. The expression of CD16 was bimodal.

FIG. 2A Characterization of the NK cells based on expressions of CD56 and CD16 on day 14. On day 14, the NK cells contained CD56$^{high}$/CD16$^{high}$ NK cells (population (i)), and CD56$^{high}$/CD16$^{low}$ NK cells (population (ii)).

FIG. 2B Characteristics of the NK cells on day 14. Expression of CD57, which is usually used as a marker of stage 5 (activated type or matured type), was not observed.

FIG. 2C Characteristics of the NK cells on day 14. They were NKG2C-positive, NKG2A-negative or lowly expressed NKG2A, and were CD94-positive.

FIG. 3 The NK cells cultured by using serum-free and CTS-added medium on day 14. The rate of the population (i) among the total NK cells could be increased.

FIG. 4 Cytotoxic activities of the populations (i) and (ii). Both the cytotoxic activities of the populations (i) and (ii) were higher than 50%.

FIG. 5 Cytotoxic activities of the populations (i) and (ii). Still higher cytotoxic activity was observed for the dinutuximab addition group.

FIG. 6 The effect of antibody drug+NK cell. As for mogamulizumab, the highest cytotoxic activity was observed for the premix group.

FIG. 7 The results of the analysis of the NK cells incubated with mogamulizumab. It could be confirmed that mogamulizumab had bound to the NK cells. Mogamulizumab could be bound to not only the NK cells of the population (i), but also those of population (ii) under the high mogamulizumab concentration conditions.

MODES FOR CARRYING OUT THE INVENTION

[NK Cell and NK Cell Population]

The present invention provides an NK cell having the following characteristic (1) or a population thereof:
(1) the NK cell is CD16-positive, highly expresses CD56, and is CD57-negative.

The NK cell or the population thereof also has the following characteristic (2):
(2) the NK cell is NKG2C-positive, is NKG2A-negative or lowly expresses NKG2A, and is CD94-positive.

The aforementioned NK cell or population thereof may further have the following characteristic (3):
(3) when the NK cell is used as effecter cells (E), and co-cultured with K562 cells as target cells (T) at a mixing ratio (E:T) of 1:1, the NK cells show a cytotoxicity of 50% or higher.

NK cells are large-sized granular lymphocytes not expressing the T cell receptor (TCR), CD3, which is a universal marker of T cell, and the B cell receptor, which is a membrane immunoglobulin, and they are usually CD16-positive, and CD56-positive in humans. Those skilled in the art can easily determine whether a cell is NK cell or not on the basis of expression pattern of cell surface markers, and so forth. NK cells have a cytotoxic activity, and presence or absence and degree of this cytotoxic activity can be measured by various known methods. The NK cells referred to herein include various NK cells such as peripheral blood NK cells, primary NK cells, cultured NK cells, activated NK cells, NK cells obtainable according to the present invention, and so forth, unless especially indicated.

<Cell Population>

The term cell population refers to a group constituted by a plurality of cells, for example, 1×10$^5$ or more of cells. A population of NK cells is a population including NK cells at a purity higher than 50% (Purity (%)=(Number of NK cells)/(Number of total cells)×100). NK cells usually constitute 10 to 30% of lymphocytes in human peripheral blood. That is, it is apparent that purity of NK cells in peripheral blood is lower than 50%. Therefore, it can be said that a population of NK cells does not exist in the nature. A population of NK cells can be prepare at various cell densities. For example, it can be prepared at a density of 1×10$^5$ cells/mL or higher.

The purity of NK cells in the population of NK cells provided by the present invention is preferably 60% or higher, more preferably 70% or higher, still more preferably 80% or higher. The number of NK cells contained in the population of NK cells is preferably 1×10$^6$ or larger, more preferably 5×10$^6$ or larger, still more preferably 1×10$^7$ or larger. The number of NK cells contained in the population of NK cells can be 1×10$^6$ to 1×10$^{10}$ cells, which is suitable for administration to a human. The cell density in the population of NK cells is 1×10$^5$ cells/mL or higher, preferably 2×10$^5$ cells/mL or higher, more preferably 5×10$^5$ cells/mL or higher, still more preferably 1×10$^6$ cells/mL or higher. As for the upper limit of the cell density, it can be, for example, 1×10$^{10}$ cells/mL or lower. The cell density in the population of NK cells can also be 1×10$^6$ to 1×10$^8$ cells/mL, which is suitable for culture or cryopreservation, or 1×10$^5$ to 1×10$^9$ cells/mL, which is suitable for administration to a human.

<Characteristic (1)>

The NK cell or those of a population thereof provided by the present highly express CD16 or lowly express CD16. The population of NK cells provided by the present invention may include both of a population of NK cells that highly express CD16, and a population of NK cells that lowly express CD16. If a cell population including both the populations is analyzed for CD16 by flow cytometry, it shows bimodal distribution. The NK cell or NK cells in the population thereof provided by the present invention highly express CD56. It is known that CD56 is an antigen useful as a marker of NK cell. Expression of CD57 is not observed in the NK cell or a population thereof provided by the present invention. CD57 is known as a marker of stage 5 (activated type or matured type).

For the markers such as CD16, positivity may be represented by +, and negativity is represented by −. For example, CD16-positive may be represented as CD16$^+$, and CD16-negative may be represented as CD16$^-$. The term positive means both of the cases that the corresponding marker is highly expressed, and lowly expressed. A highly expressing property may be represented as high or bright. For example, a property of highly expressing CD16 may be represented as CD16$^{high}$ or CD16$^{bright}$. A lowly expressing property may be represented as low or dim. For example, a property of lowly expressing CD16 may be represented as CD16$^{low}$ or CD16$^{dim}$.

Such positive, negative, highly expressing, and lowly expressing properties can be determined on the basis of a chart obtained by flow cytometry. Although the positions on the chart may vary depending on the setting of voltage and sensitivity in the instrument, used antibody clone, staining conditions, used dye, and so forth, those skilled in the art can appropriately classify the properties on the obtained chart without dividing a cell population that should be recognized as a single group.

Whether a cell is positive or negative for expression of a target marker can be determined by using a negative control using an isotype control antibody. The isotype control antibody is an antibody that does not react with a specific antigen. In experiments using antibodies, a background may generally be produced by nonspecific binding with a protein other than the target, or binding with the Fc receptor on the cell surfaces. By comparison with a system using an antibody that serves as a negative control, it can be clarified whether the reaction of the primary antibody with the target antigen is specific. The influence of the background is also eliminated, and therefore strength of signal can be correctly determined.

Degree of expression of a target marker (lowly expressed or highly expressed) can be determined by comparison with result of measurement performed for a control cell under the same conditions. Examples of the control cell are NK cells obtained from peripheral blood and not substantially cultured, such as the primary NK cells mentioned in the section of Examples of this specification.

As for degree of expression of CD16, for example, expression amount of CD16 in a certain population of NK cells determined by using flow cytometry can be compared with expression amount of CD16 in a population of NK cells obtained from peripheral blood and not substantially cultured (control, known to highly express CD16), and when the expression amount is comparable to that of the control, they can be determined to have a highly expressing property, or when the expression amount is lower than that of the control, they can be determined to have a lowly expressing property.

As for expression of CD56, it is generally understood that NK cells at stage 4 (young NK cells differentiated from stem cells via the stages of pro-NK, pre-NK, and immature-NK) are $CD56^{bright}$ and NK cells at stage 5 (if the transcription factor MCM4 is activated in NK cells at stage 4, the NK cells differentiate into NK cells at stage 5) are $CD56^{dim}$. Therefore, degree of expression of CD56 in a certain population of NK cells may be determined by comparison with at least one of a population of NK cells at stage 4, and a population of NK cells at stage 5.

The characteristics of conventionally known NK cells and the NK cells obtained by the present invention are summarized below (refer to Non-patent documents 1 and 2).

NKG2A, and is CD94-positive. The properties of NKG2A-negative to lowly expressing NKG2A, and expression of CD94 are observed for most NK cells. CD94 binds with one of the NKG2 family molecules via a disulfide bond to form a receptor for MHC class I molecules. It is known that NKG2C is mainly expressed in NK cells, and participates in the activation of NK cells, and a CD94/NKG2C heterodimer functions as an activated receptor. The CD94/NKG2A heterodimer is an inhibitory receptor for MHC class I molecules. The expression that a cell is NKG2A-negative or lowly expresses NKG2A means that the cell shows no expression of NKG2A (negative), very weakly expresses NKG2A, or lowly expresses NKG2A.

According to the investigations of the inventors of the present invention, the NK cell provided by the present invention or a population thereof has been found to be $CD94^{++}$, $KIR^+$, and $perforin^{+++}$ by comparison with the NK cells reported in Non-patent document 1 (refer to a to d mentioned above).

The NK cell or a population thereof provided by the present invention can be distinguished from known NK cells or a population thereof on the basis of the following characteristic (2-1) in addition to or instead of the characteristic (2). (2-1) It is KIR (killer cell immunoglobulin-like receptor(s))-positive.

The term KIR(s)-positive means that the cell is positive for at least one selected from the group consisting of KIR2DL1, KIR2DL2, KIR2DL3, KIR2DL4, KIR2DL5, KIR3DL1, KIR3DL2, KIR3DL3, KIR2DS1, KIR2DS2, KIR2DS3, KIR2DS4, KIR2DS5, and KIR3DS1.

The NK cell or a population thereof provided by the present invention can be distinguished from known NK cells or a population thereof on the basis of the following characteristic (2-2) in addition to or instead of the characteristic (2). (2-2) It shows one, preferably two, of properties selected

TABLE 1

|  | NK cell at stage 4 | NK cell of the present invention | | NK cell at stage 5 |
|---|---|---|---|---|
|  |  | (i) | (ii) |  |
| Localization etc. | Secondary lymph gland | Artificially produced | | Circulating blood |
| CD16 | Positive (low expression) | Positive (high expression) | Positive (low expression) | Positive (high expression) |
| CD56 | Positive (high expression) | Positive (high expression) | Positive (high expression) | Positive (low expression) |
| CD57 | Negative | Negative | Negative | Positive |
| Cytotoxicity | Low | High | High | High |

The above table conceptually summarizes results of evaluation of NK cells for CD16 and CD56 expressions observed on charts obtained by flow cytometry. The correspondences of the characteristics of expressions in the cells reported in the drawing of Non-patent document 1 are as the following a to d.
a: $CD56^{bright}$, $CD94^{+++}$, $KIR^-$, $CD16^-$, $perforin^{+-}$,
b: $CD56^{dim}$, $CD94^{++}$, $KIR^-$, $CD16^{+-}$, $perforin^+$,
c: $CD56^{dim}$, $CD94^+$, $KIR^-$, $CD16^+$, $perfori^{++}$
d: $CD56^{dim}$, $CD94^{+-}$, $KIR^+$, $CD16^{++}$, $CD57^+$, $perforin^{+++}$ Primary NK cells obtained from peripheral blood highly express CD16. It is generally known that NK cells that highly express CD16 are $CD56^{dim}$ and $CD57^+$. NK cells that are $CD16^{high}$, $CD56^{high}$ and $CD57^-$ are not reported so far.
<Characteristic (2)>

The NK cell provided by the present invention is also NKG2C-positive, is NKG2A-negative or lowly expresses from the group consisting of properties of NKp44-positive, highly expressing NKp30, and highly expressing NKp46, or preferably all of them.

Primary NK cells are usually negative for NKp44 expression. NKp30 is an NK-specific target receptor that induces non-MHC-dependent cell injury, and is one of the natural cytotoxicity receptors (NCRs) identified so far, which include NKp46 and NKp44. It is known that the expression of NKp30 occurs in parallel with that of NKp46, and NK cells that are $NKp46^{bright}$ are also $NKp30^{bright}$. It is also known that the property of $NKp30^{bright}$ correlates to high cytotoxicity. As for the fact that the NK cell or a population thereof provided by the present invention is characterized by the characteristic (2-2), Example 1 mentioned in this specification and FIG. 1 can be referred to.

As for the surface marker expression patterns for each of the differentiation stages of NK cells, the following reference can be referred to.

Non-patent document 3: Luetke-Eversloh M., M. Killig, C. Romagnani, 2013, Signatures of human NK cell development and terminal differentiation, Front. Immunol., 4:499, PubMed, Google Scholar <Characteristic (3)>

The NK cell or a population thereof provided by the present invention can show high cytotoxic activity. The term cytotoxic activity refers to an ability of an objective cell (effecter cell, E) for lysing a target cell (T), unless especially indicated. Cytotoxic activity can be represented by percentage (%) of the target cells killed by the effecter cells, and can be obtained in accordance with the following equation.

(Number of cell death observed in co-culture with effecter cells−Number of natural cell death (negative control))/(Maximum number of cell death(positive control)−Number of natural cell death(negative control))×100

At the time of the measurement of cytotoxic activity, in general, the mixing ratio of effecter cells and target cells (E:T), and time of co-culture of effecter cells and target cells can be appropriately chosen depending on types and strength of the activity of the cells to be used. When NK cells are used as the effecter cells, the target cell may be the K562 cell, acute myeloid leukemia cell, or chronic myeloid leukemia cell, but it is not limited to these. The effecter cells and target cells, as well as living cells and dead cells can be distinguished and quantified by using a reagent such as an antibody labeled with a radioactive substance, fluorescent dye, or the like. Cytotoxic activity obtained by using NK cells as the effecter cells for, for example, the K562 cells as the target cells can be measured under the conditions of E:T=1:0.05 to 10, preferably 1:0.1 to 5, and an incubation time of 0.5 to 18 hours, preferably 1 to 12 hours.

When the NK cell or a population thereof provided by the present invention is co-cultured with the K562 cells as the target cells at an E:T ratio of 1:1 for 1 to 3 hours, more specifically 2 hours, cytotoxic activity thereof is 50% or higher, preferably 60% or higher, more preferably 70% or higher.

Primary NK cells obtained from peripheral blood show low cytotoxic activity. NK cells that are $CD16^{high}$, $CD56^{high}$ and $CD57^{-}$, and show high cytotoxic activity have not been reported so far.

[Preparation Method of NK Cell or Population Thereof]

The present invention provides a method for preparing the aforementioned NK cell or a population thereof, which comprises the following step:

the step of culturing a population of primary NK cells in a medium containing IL-2.

<Primary NK Cells>

In the preparation method of the present invention, a population of primary NK cells can be obtained by the step of separating monocytes from hemocyte cells extracted from a test subject. The hemocyte cells may be extracted from peripheral blood, cord blood, bone marrow, and/or lymph gland. The hemocyte cells may be extracted from peripheral blood by the apheresis method.

In the preparation method of the present invention, a population of primary NK cells may be prepared form hematopoietic stem cells derived from stem cells selected from the group consisting of embryonic stem cells, adult stem cells, and artificial pluripotent stem (iPS) cells, and at least one kind of cells selected from the group consisting of hematopoietic stem cells derived from cord blood, hematopoietic stem cells derived from peripheral blood, hematopoietic stem cells derived from bone marrow blood, cord blood monocytes, and peripheral blood monocytes. The test subject as a donor of a population of primary NK cells may be a patient himself or herself as a recipient, a closely related person of the patient, or a person not having blood relationship with the patient. The test subject may be a healthy subject, or a patient suffering from a disease. The NK cells may be derived from a donor whose major histocompatibility antigen (MHC) and killer immunoglobulin-like receptor (KIR) do not conform to those of the recipient.

In the preparation method of the present invention, T cells may be removed from the population of primary NK cells. T cells may be removed by the step of removing CD3-positive cells.

The preparation method of NK cells of the present invention may include the step of removing hemopoietic precursor cells from a population of primary NK cells. The step of removing hemopoietic precursor cells from a cell population including NK cells may be attained by the step of removing CD34-positive cells.

A population of primary NK cells can be prepared by using various procedures known to those skilled in the art. For example, when monocytes are collected from blood such as cord blood and peripheral blood, the specific gravity centrifugation method can be used. NK cells can also be collected by using immunomagnetic beads. Further, a population of primary NK cells can also be isolated and identified by using FACS (fluorescence activated cell sorter) or flow cytometer after performing immunofluorescence staining using a specific antibody for a cell surface marker. A population of primary NK cells may also be prepared by separating and removing cells expressing the cell surface antigens CD3 and/or CD34 by using immunomagnetic beads, which include Dynabeads (trademark) produced by Dynal and sold by Invitrogen and CliniMACS (trademark) of Miltenyi Biotech, but are not limited to these. T cells and/or hemopoietic precursor cells may be selectively injured or killed by using a specific binding partner for the T cells and/or hemopoietic precursor cells. The step of removing T cells may be a step of removing T cells together with cells of other type or types, for example, hemopoietic precursor cells, B cells, and/or NKT cells. The step of removing hemopoietic precursor cells may be a step of removing hemopoietic precursor cells together with cells of other type or types, for example, T cells, B cells, and/or NKT cells.

<Medium>

The medium for cell culture used for culturing a population of primary NK cells may be the KBM501 medium (Kohjin Bio, containing 1,750 JRU/ml of IL-2, for primary culture of human NK cells), CellGro SCGM medium (CellGenix, sold by Iwai Chemicals), X-VIV015 medium (Lonza, sold by Takara Bio), Cosmedium 008 (Cosmo Bio, containing 1,750 JRU/ml of IL-2, for primary culture of human NK cells), CTS AIM V Medium, Gibco™ CTS™ AIM V™ Medium (Thermo Fisher Scientific, serum-free medium of known composition for proliferating and manipulating T cells and dendritic cells), CTS OpTmizer T Cell Expansion Basal Medium (Thermo Fisher Scientific, for growing and proliferating human T lymphocytes), IMDM, MEM, DMEM, RPMI-1640, or the like, but it is not limited to these.

The medium may contain interleukin-2 (IL-2) at such a concentration that the object of the present invention can be attained. The concentration of IL-2 may be 2500 to 2813 IU/mL. IL-2 preferably has the amino acid sequence of human IL-2, and it is preferably prepared by a recombinant DNA technique in view of safety. The concentration of IL-2 may be represented with the Japanese standard unit (JRU) or international unit (IU). Since 1 IU is about 0.622 JRU, the concentration of 1750 JRU/mL in the existing media corresponds to about 2813 IU/mL.

The medium may contain autoserum of the test subject, human AB type serum available from BioWhittaker or the like, or donated human blood serum albumin available from the Japanese Red Cross Society. Autoserum and human AB type serum are preferably contained at a concentration of 1 to 10%, and donated human blood serum albumin is preferably contained at a concentration of 1 to 10%.

The medium may contain appropriate protein, cytokine, antibody, compound, and other ingredients on condition that the amplification effect for NK cells is not degraded. The cytokine may be interleukin 3 (IL-3), interleukin 7 (IL-7), interleukin 12 (IL-12), interleukin 15 (IL-15), interleukin 21 (IL-21), stem cell factor (SCF), and/or FMS-like tyrosine kinase 3 ligand (Flt3L). IL-3, IL-7, IL-12, IL-15, IL-21, SCF, and Flt3L preferably have the amino acid sequences of those of humans, and they are preferably prepared by a recombinant DNA technique in view of safety.

The medium is preferably a serum-free medium. The serum-free medium preferably contains serum albumin, transferrin, and insulin. Serum-free media for culturing lymphocytes are developed and marketed, and they can be used for the present invention. One of the preferred examples of the serum-free medium is a basal medium to which CTS Immune Cell SR (Thermo Fisher Scientific) marketed as a composition for supporting proliferation of human T cells is added.

Although medium exchange may be performed at any time after the start of the culture on condition that a desired cell number of NK cells can be obtained, it is preferably performed every 3 to 5 days.

The culture vessel used for the culture may be a commercially available dish, flask, plate, or multi-well plate, but it is not limited to these. Although the culture conditions are not particularly limited on condition that the proliferation effect for NK cells is not degraded, culture conditions of 37° C., 5% $CO_2$, and saturated steam atmosphere are common. A longer period of the culture in the medium provides more NK cells, and therefore is more advantageous. The culture period is not particularly limited on condition that NK cells are proliferated to a desired cell number.

A population of the predetermined NK cells obtained by the culture may contain NK cell precursors, T cells, NKT cells, hemopoietic precursor cells, and so forth in addition to the objective NK cells. After the culture, the objective NK cell or a population thereof may be selected by using, for example, specific gravity centrifugation, immunomagnetic beads, FACS, flow cytometry, and so forth. For example, by using anti-CD3 antibody, anti-CD16 antibody, anti-CD34 antibody, anti-CD56 antibody, anti-CD69 antibody, anti-CD94 antibody, anti-CD107a antibody, anti-KIR3DL1 antibody, anti-KIR3DL2 antibody, anti-KIR2DL3 antibody, anti-KIR2DL1 antibody, anti-KIR2DS1 antibody, anti-KIR2DL5 antibody, anti-NKp46 antibody, anti-NKp30 antibody, anti-NKG2D antibody, or the like, the objective NK cell or a population thereof may be selectively separated. The antibody may be a monoclonal antibody, polyclonal antibody, or the like. Selection of the objective NK cell or a population thereof may be performed by selectively removing T cells, NKT cells, hemopoietic precursor cells, and other types of cells.

[Use of NK Cell or Population Thereof]

The present invention provides a pharmaceutical composition containing a population of NK cells and an additive acceptable for a drug. The present invention also provides a pharmaceutical composition containing a population of NK cells and a therapeutically effective amount of antibodies. Examples of additive acceptable for a drug include, for example, isotonic agent, pH adjustor, buffering agent, stabilizer, cryoprotective agent, antibiotic, and so forth. Specific examples include water, ethanol, sodium chloride, glucose, albumin, and so forth. The population of NK cells contained in the pharmaceutical composition of the present invention is preferably a population of the aforementioned NK cell provided by the present invention. The NK cells of the population of NK cells contained in the pharmaceutical composition of the present invention may highly expresses CD16, and in any case, a population of NK cells having higher cytotoxic activity is more preferred.

The antibody used for the pharmaceutical composition of the present invention is preferably an antibody usable as antibody drug. An antibody that can induce antibody-dependent cellular cytotoxicity (ADCC) is preferred. Although the antibody used for the pharmaceutical composition of the present invention may be any of mouse antibody, chimeric antibody, humanized antibody, and human antibody, it is preferably a humanized antibody or human antibody. The antibody to be used may be modified or may be prepared by the POTELLIGENT technology (elimination of fucose of the Fc region of IgG).

Specific examples of antibody that is used as antibody drug and can be used for the pharmaceutical composition of the present invention include ibritumomabtiuxetan, iodine131, catumaxomab, blinatumomab, muromonab-CD3, abciximab, rituximab, basiliximab, infliximab, cetuximab, brentuximab, siltuximab, dinutuximab, obiltoxaximab, daclizumab, palivizumab, trastuzumab, gemtuzumab, alemtuzumab, omalizumab, efalizumab, bevacizumab, natalizumab, tocilizumab, ranibizumab, eculizumab, certolizumabpegol, mogamulizumab, pertuzumab, trastuzumab, obinutuzumab, vedolizumab, pembrolizuma, idarucizumab, mepolizumab, elotuzumab, daratumumab, ixekizumab, reslizumab, adalimumab, panitumumab, golimumab, ustekinumab, canakinumab, ofatumumab, denosumab, ipilimumab, belimumab, raxibacumab, ramucirumab, nivolumab, secukinumab, evolocumab, alirocumab, and necitumumab.

The antibody used for the pharmaceutical composition of the present invention preferably shows high affinity for CD16. In the pharmaceutical composition of the present invention, at least a part of the antibody preferably binds to the NK cells. According to the investigations of the inventors of the present invention, when mogamulizumab prepared by the POTELLIGENT technology was used as the antibody, a higher cytotoxic activity was observed in a co-culture system obtained by mixing NK cells and the antibody beforehand, washing the NK cells, and then co-culturing the NK cells with the target cells (antibody not binding to the cells was removed) compared with a system in which the antibody was added to a co-culture of the NK cells and the target cells. However, when dinutuximab was used under the same conditions, the effect of mixing NK cells and antibody beforehand was not observed. This suggests that if an antibody showing higher affinity for CD16 is mixed with NK cells beforehand, the antibody binds to NK cells, and therefore higher ADCC activity can be obtained. It is considered that, by choosing the conditions, the same effect can also be obtained with dinutuximab.

The pharmaceutical composition of the present invention may be prepared upon use. For example, a population of NK cells and antibodies may be maintained in a state that they are contained in separate containers, and the pharmaceutical composition of the present invention can be prepared by mixing them immediately before to several hours before the administration to an object.

The pharmaceutical composition of the present invention may be prepared through a step of mixing a population of NK cells and antibodies, and then removing the antibodies not binding to the NK cells. That is, according to a preferred embodiment of the pharmaceutical composition of the present invention, it contains NK cells and antibodies, and the antibodies bind to the NK cell, and it does not substantially contain the antibodies not binding to the NK cells.

It is supposed that many of antibody drugs exhibit an antitumor effect based on the ADCC activity after intravenous administration thereof. When the ADCC activity is exhibited, monocytes, macrophages and neutrophiles are also recruited in addition to NK cells. It is considered that the effecters other than the NK cells exhibit the ADCC activity without distinguishing normal cells and cancer cells, and it also led to expression of side reactions. According to the present invention, NK cells and antibodies are mixed before the administration, and NK cells are thereby made to carry the antibodies beforehand. Accordingly, the effecter is limited to the NK cells, therefore the amount of the antibodies to be administered can be reduced, and it is considered that it is also very effective for reducing side reactions.

The pharmaceutical composition of the present invention may be administered to a patient who has an HLA genotype different from that of the NK cells prepared by the preparation method of the present invention.

The pharmaceutical composition is typically in the form of a suspension in which the NK cells are suspended in a solution. The solution for suspending the NK cells is usually, for example, a protection solution for freezing containing DMSO, physiological saline, phosphate buffered saline (PBS), medium, serum, or the like. The solution may contain a pharmacologically acceptable carrier for drugs and quasi drugs.

The pharmaceutical composition of the present invention may be used in order to treat an infectious disease or cancer. The pharmaceutical composition of the present invention is also applicable to therapeutic treatment and/or prophylactic treatment of various diseases susceptive to NK cells. Examples of such diseases includes, for example, mouth cancer, gallbladder cancer, cholangioma, lung cancer, liver cancer, colon cancer, kidney cancer, vesical cancer, leukemia, infectious disease caused by viruses, bacteria, etc., but they are not limited to these. The cell therapy of the present invention may be carried out independently, or may be carried out in combination with surgical therapy, chemotherapy, radiotherapy, use of antibody drug, and so forth. In a cell therapy using the pharmaceutical composition of the present invention, NK cells may be administered, for example, intravenously, intraarterially, subcutaneously, intraperitoneally, or the like.

The pharmaceutical composition of the present invention is preferably prepared under conditions that conform to the regulations for production control and quality control of drugs and quasi drugs (Good Manufacturing Practice, GMP) and standards of production control and quality control for medical supply for regeneration medicine etc. (Good Gene, Cellular, and Tissue-based Products Manufacturing Practice, GCTP).

In the present invention, extraction of the whole blood as cord blood or peripheral blood, preparation of autoserum, preparation of monocytes from the whole blood, measurement of cells number of monocytes before and after culture, measurement of the percentages of NK cells, T cells, hemopoietic precursor cells, and cells of other types among the monocytes before and after the culture, calculation of the amplification magnification of NK cells, and statistical analysis about measurement error or significance may be carried out by using any of the methods well known to those skilled in the art.

The examples of the present invention explained below are mentioned only for the purpose of exemplification, and do not limit the technical scope of the present invention. The technical scope of the present invention is defined only by the descriptions of the claims. The present invention may be implemented with any alterations such as addition, deletion and substitution of the elements of the present invention on condition that such alterations do not depart from the scope of the present invention.

EXAMPLES

Example 1

Blood was collected from a healthy volunteer, and peripheral blood monocytes were obtained by separation using Ficoll (GE Healthcare, 17144002). CD3 beads*[1] were added to the obtained peripheral blood monocytes, and suspended therein, the suspension was incubated at 4° C. for 15 minutes, a separation buffer 1*[2] was added, and the cells and the beads were sufficiently suspended, and the resulting suspension was centrifuged at 300×g for 10 minutes. The supernatant was removed, the residue was suspended in 1 mL of the separation buffer, the resulting suspension was added to LD Column (Miltenyi Biotech, 130-042-901) wetted beforehand with 2 mL of the separation buffer, and the eluate from the LD Column was collected. The separation buffer (1 mL) was further added to the LD Column, and the eluate was collected. Then, the column was washed twice, and the cell numbers in the collected liquids were counted, and the total cell number was calculated. The collected liquids were centrifuged at 500×g for 5 minutes, the supernatant was removed, and the cells were suspended in the NK medium I*[3] at a density of $5 \times 10^5$ cells/mL. A part of the cells was collected for flow cytometry measurement (the cells collected here are referred to as "Primary NK"), and the remaining cells were cultured. The culture was performed by using a 6-well plate (Thermo Fisher Scientific, 140675) or T-75 flask (Thermo Fisher Scientific, 156499) in a $CO_2$ incubator (37° C., 5% $CO_2$). Apart of the culture medium was taken on day 5 and day 9 of the culture, the cell numbers were counted, and the NK medium I was added to obtain a cell density of $5 \times 10^5$ cells/mL. The cells were collected on day 14 (the cells collected here are referred to as "Day 14"), and the cell surface antigens were measured with a flow cytometer by using a part of the cells. The remaining cells were suspended in STEM-CELLBANKER GMP Grade (Takara Bio, CB045), and then stored at −80° C.

*[1]: CliniMACS CD3, Miltenyi Biotech, catalog number 130-017-601 (5μ per $1 \times 10^7$ of cells)
*[2]: PBS containing 0.5% human AB type serum (obtained by inactivating Cosmo Bio, 12181301 at 56° C. for 30 minutes) and 2 mM EDTA (Thermo Fisher Scientific, 15575-020)
*[3]: COSMEDIUM 008 (Cosmo Bio, COS-008) containing 5% of human AB type serum (obtained by inactivating Cosmo Bio, 12181301 at 56° C. for 30 minutes)

The collected cells were stained with the following antibodies. That is, the cells were stained with BV421-labeled anti-human CD56 antibody (Biolegend, 318328), PerCP/C5.5-labeled anti-human CD3 antibody (Biolegend, 300430), APC-labeled anti-human NKp30 antibody (Biolegend, 325209), PE-labeled anti-human NKp44 antibody (Biolegend, 325107), FITC-labeled anti-human NKp46 antibody (Biolegend, 331921), PE-Cy7-labeled anti-human NKG2D antibody (Biolegend, 320811), PE-Cy7-labeled anti-human CD16 antibody (Biolegend, 302015), APC-labeled anti-human CD69 antibody (Biolegend, 310910), FITC-labeled anti-human CD94 antibody (Biolegend, 305504), FITC-labeled anti-human CD14 antibody (Biolegend, 325604), PE-labeled anti-human NKG2C antibody (R&D, FAB138P), APC-labeled anti-human NKG2A antibody (Miltenyi Biotec, 130-098-809), PerCP Cy5.5-labeled anti-human CD94 antibody (Biolegend, 305514), and APC-labeled anti-human CD57 antibody (Biolegend, 359610) at a concentration of 1 µg/mL at 4° C. for 30 minutes, and then centrifuged (500×g, 5 minutes, 4° C.), the supernatant was removed, the cells were suspended in PBS (Wako Pure Chemical Industries), measurement was performed by using a flow cytometer (BD LSRFortessa, BD Biosciences), and the results were analyzed by using the FlowJo software (TreeStar).

The results are shown in FIG. 1. The NK cells on day 14 showed the characteristics of so-called highly activated NK cells that strongly express activated type receptors such as NKp46, NKp30, and NKG2D. On the other hand, expression of CD16 thereof was bimodal.

Example 2

Cells were prepared by the method described in Example 1. A part of the cells was collected at the times of the start of the culture and at the end of the culture (day 14 of the culture), and the cell surface antigens were measured with a flow cytometer.

About $1 \times 10^5$ of the collected cells were stained at 4° C. for 30 minutes with BV421-labeled anti-human CD56 antibody, PerCP/C5.5-labeled anti-human CD3 antibody, PE-Cy7-labeled anti-human CD16 antibody, APC-labeled anti-human CD69 antibody, and FITC-labeled anti-human CD14 antibody at a concentration of 1 µg/mL, and then centrifuged (500×g, 5 minutes, 4° C.), the supernatant was removed, the cells were suspended in an optimum volume of PBS, measurement was performed by using a flow cytometer (BD LSRFortessa, BD Biosciences), and the results were analyzed by using the FlowJo software. The CD3-negative and CD56-positive cells were recognized as NK cells, and developed for CD16 and CD56 to analyze the expression of CD16 on the NK cells.

The results are shown in FIGS. 2A to 2C. The NK cells on day 14 contained $CD56^{high}/CD16^{high}$ NK cells (population (i)) and $CD56^{high}/CD16^{low}$ NK cells (population (ii)) (FIG. 2A), and expression of CD57, which is usually used as a marker of stage 5 (activated type or matured type) was not observed (FIG. 2B). It was found that the NK cells on day 14 further have the characteristics of NKG2C-positive, NKG2A-negative to lowly expressing NKG2A, and CD94-positive (FIG. 2C).

Example 3

Cells were prepared by the method described in Example 1 with a partial modification. Specifically, culture was performed by using a separation buffer 2*[4] and an NK medium II*[5]. A part of the cells was collected at the times of the start of the culture and at the end of the culture (day 14 of the culture), and measurement and analysis were carried out according to the methods described in Example 2.

*4: PBS containing 0.5% CTS™ Immune Cell SR (Thermo Fisher Scientific, A25961-01, henceforth referred to as CTS), and 2 mM EDTA
*5: Cosmedium 008 medium (Cosmo Bio, COS-008) containing 5% of CTS The results are shown in FIG. 3. The ratio of the population (i) to the total NK cells could be increased by use of the serum-free medium containing CTS.

Example 4

<<Preparation of K562 (Target Cells)>>

K562 cells (human chronic myeloid leukemia cell strain) were prepared at a density of $1 \times 10^6$ cells/ml in the RPMI1640 medium (Wako Pure Chemical Industries, 189-02025) containing 10% FBS (Nichirei Bioscience, 171012-500ML), 100 units of penicillin, and 100 µg/mL of streptomycin (Nacalai Tesque, 26253-84) (henceforth referred to as 10% FBS/RPMI1640). To the prepared K562 cells, DiOC18 (Sigma, D4292-20MG) was added at a final concentration of 30 µM, and the reaction was allowed at 37° C. for 10 minutes. The cell suspension was centrifuged (400×g, 5 minutes, room temperature), then the supernatant was removed, 10% FBS/RPMI1640 was added to the cells, and the cells were suspended in the medium. This washing process was repeated 3 times, and a cell suspension at a density of $2 \times 10^6$ cells/mL was finally prepared by using 10% FBS/RPMI1640.

<<Preparation of NK Cells (Effecter Cells)>>

Cells obtained from a healthy volunteer by the method described in Example 1 were suspended in 10% FBS/RPMI1640 after the collection and washing, and adjusted to a density of $1 \times 10^6$ cells/ml with the same medium. The prepared cell suspension was subjected to staining with PE-Cy7-labeled anti-human CD16 antibody (1 µg/mL) at 4° C. for 30 minutes, and then centrifuged (500×g, 5 minutes, 4° C.), and the supernatant was removed. The cells were suspended by using 10% FBS/RPMI1640, and adjusted to a density of $2 \times 10^7$ cells/ml with the same medium, the cell surface antigens were measured with a flow cytometer (Cell Sorter SH800, SONY) to confirm degree of CD16 expression. $CD16^{high}$ NK cells and $CD16^{dim}$ NK cells were sorted with the same cell sorter, and collected respectively in 15-ml conical tubes filled with 7 ml of 10% FBS/RPMI1640. After the collection, the cell suspension was centrifuged (500×g, 5 minutes, 4° C.), the supernatant was removed, then the cells were suspended in 10% FBS/RPMI1640, and the cell suspension was adjusted to a density of $2 \times 10^6$ cells/ml with the same medium.

<<Measurement of Cytotoxic Activity>>

A group of NK cells not sorted and K562 cells, a group of $CD16^{high}$ NK cells and K562 cells, a group of $CD16^{dim}$ NK cells and K562 cells, and groups of NK cells of respective types, 6 groups in total, as well as a group of only K562 cells as a negative control and a group of K562 cells fixed with 10% formalin as a positive control were prepared. The NK cells and K562 cells were added to a 96-well plate and mixed at a cell number ratio of 1:1, and co-cultured at 37° C. for 2 hours. This culture was performed by first adding the K562 cells to the plate, then adding 200 µg/ml APC-labeled anti-human CD107a antibody*[6] (Biolegend, 328620) at a final concentration of 1 µg/ml, and finally adding each type of NK cells. After the culture, the culture medium was centrifuged (500×g, 5 minutes, 4° C.), the supernatant was removed, a 7-AAD solution (Beckman Coulter, A07704) diluted with PBS was added to suspend the cells, and the cell suspension was incubated at room temperature for 10 minutes. Measurement was performed by using a flow cytometer (BD LSR Fortessa, BD Biosciences), and the results were analyzed with the FlowJo software.

*6: Since CD107a exists in intracellular granules of NK cells and moves to cell membrane surfaces at the time of degranulation (release of perform and granzyme), positivity for CD107a indirectly indicates that NK has attacked the object.

Cytotoxic activity was calculated in accordance with the following equation. Cytotoxic activity was calculated in the same manner also in the following examples.

(Number of cell death of target cells observed after incubation with effecter cells−Number of natural cell death(negative control))/(Maximum number of cell death(positive control)−Number of natural cell death(negative control))×100

<<Results>>

The results are shown in FIG. 4. Both the population (i) and the population (ii) showed cytotoxic activity higher than 50%.

Example 5

<<Preparation of IMR32 Cells (Target Cells)>>

IMR32 cells (human MYCN-amplified neuroblastoma cell strain) were prepared at a density of $1 \times 10^6$ cells/ml in 10% FBS/RPMI1640. DiOC18 (Sigma, D4292-20MG) was added to the prepared K562 cells at a final concentration of 30 μM, and the reaction was allowed at 37° C. for 10 minutes. The cell suspension was centrifuged (400×g, 5 minutes, room temperature), then the supernatant was removed, and 10% FBS/RPMI1640 was added to the cells to suspend them. This washing process was repeated 3 times, and a cell suspension was finally prepared at a density of $2 \times 10^6$ cells/mL by using 10% FBS/RPMI1640.

<<Preparation of NK Cells (Effecter Cells)>>

Cells obtained from a healthy volunteer by the method described in Example 1 were suspended in 10% FBS/RPMI1640 after the collection and washing, and adjusted to a density of $1 \times 10^6$ cells/ml with the same medium. The prepared cell suspension was subjected to staining with PE-Cy7-labeled anti-human CD16 antibody (1 μg/mL) at 4° C. for 30 minutes, and then centrifuged (500×g, 5 minutes, 4° C.), and the supernatant was removed. The cells were suspended in 10% FBS/RPMI1640, and the density was adjusted to $2 \times 10^7$ cells/ml with the same medium, the cell surface antigens were measured with a flow cytometer (Cell Sorter SH800, SONY) to confirm degree of CD16 expression. $CD16^{high}$ NK cells and $CD16^{dim}$ NK cells were sorted with the same cell sorter, and collected respectively in 15-ml conical tubes filled with 7 ml of 10% FBS/RPMI1640. After the collection, the cell suspension was centrifuged (500×g, 5 minutes, 4° C.), the supernatant was removed, then the cells were suspended in 10% FBS/RPMI1640, and the density was adjusted to $2 \times 10^6$ cells/ml with the same medium.

<<Measurement of Cytotoxic Activity>>

A group of NK cells not sorted and IMR32 cells, a group of $CD16^{high}$ NK cells and IMR32 cells, a group of $CD16^{dim}$ NK cells and IMR32 cells, and groups of NK cells of each type, 6 groups in total, as well as of a group of only IMR32 cells as a negative control and a group of IMR32 cells fixed with 10% formalin as a positive control were prepared. The NK cells and IMR32 cells were added to a 96-well plate and mixed at a cell number ratio of 1:1, and co-cultured at 37° C. for 2 hours.

This culture was performed by adding IMR32 cells to the plate first, then adding 1 μl each of dinutuximab (Unituxin (trade name), United Therapeutics) prepared at 100 μg/ml with PBS, adding 200 μg/ml APC-labeled anti-human CD107a antibody at a final concentration of 1 μg/ml, and finally adding each type of NK cells. After the co-culture, the culture medium was centrifuged (500×g, 5 minutes, 4° C.), the supernatant was removed, then a 7-AAD solution (Beckman Coulter, A07704) diluted with PBS was added to suspend the cells, and the cell suspension was incubated at room temperature for 10 minutes. Measurement was performed by using a flow cytometer (BD LSR Fortessa, BD Biosciences), and the results were analyzed with the FlowJo software.

<<Results>>

The results are shown in FIG. 5. Still higher cytotoxic activity was observed for the dinutuximab addition group.

Example 6

<<Preparation of Cells<<

NK cells obtained by the method described in Example 1 were suspended in the NK medium I containing mogamulizumab (POTELIGEO (registered trademark) Injection 20 mg, Kyowa Kirin) at a concentration of 4 μg/mL, and the cell suspension was incubated at 37° C. for 20 minutes. The cell suspension was centrifuged (500×g, 5 minutes, room temperature), then the supernatant was removed, 10% FBS/RPMI1640 was added to the cells to suspend them, then the cell suspension was centrifuged (500×g, 5 minutes, room temperature), the supernatant was removed, and a cell suspension was prepared at a density of $2 \times 10^6$ cells/mL with 10% FBS/RPMI1640 to prepare NK+mogamulizumab (premix).

DiOC18 (Sigma, D4292-20MG) was added to the Hut78 cells (human T lymphoma cell strain) at a final concentration of 1 μM, and the reaction was allowed at 37° C. for 10 minutes. The cell suspension was centrifuged (400×g, 5 minutes, room temperature), then the supernatant was removed, and 10% FBS/RPMI1640 was added to the cells to suspend them. This washing process was repeated 3 times, and a cell suspension was finally prepared at a density of $2 \times 10^6$ cells/mL by using 10% FBS/RPMI1640.

<<Measurement of Cytotoxic Activity>>

A group comprising NK cells and Hut 78 cells at a ratio of 1:5 (cell number ratio), a group comprising NK cells and Hut 78 cells at a ratio of 1:5 (cell number ratio) and containing mogamulizumab at a final concentration of 4 μg/mL, and a group comprising NK+mogamulizumab (premix) and Hut 78 cells at a ratio of 1:5 (cell number ratio), 3 groups in total, were prepared. The cells were added to a 96-well plate at a cell number ratio of 1:5, mixed, and co-cultured at 37° C. for 2 hours. A group comprising only the Hut 78 cells as a negative control, and a group comprising Hut 78 fixed with 10% formalin as a positive control were also prepared. After co-culture for 2 hours, each culture was centrifuged (500×g, 5 minutes, room temperature), the supernatant was removed, a 7-AAD solution (Beckman Coulter, A07704) diluted 6 times with PBS was added to the cells in a volume of 60 μl/well to suspend them, and the suspension was incubated at room temperature for 10 minutes. Measurement was performed by using a flow cytometer (BD LSRFortessa, BD Biosciences), and the results were analyzed by using the FlowJo software.

<<Preparation of IMR32 Cells and Measurement of Cytotoxic Activity>>

Experiments were performed in the same manners as those of the aforementioned experiments using Hut78, except that the cell strain used was IMR32, the antibody used was dinutuximab, and the cell number ratio of NK cells and the tumor cells was 1:10.

<<Results>>

The results are shown in FIG. 6. As for mogamulizumab, the highest cytotoxic activity was observed for the NK+mogamulizumab (premix) group. One of action mechanisms of many antibody drugs is the antibody-dependent cell cytotoxicity (ADCC) activity of NK cells, and effectiveness of mixing NK cells and an antibody drug beforehand was suggested.

Example 7

NK cells obtained by the method described in Example 1 were frozen by using STEM-CELLBANKER GMP Grade (Takara Bio, CB045), then thawed, and cultured overnight by using the NK medium II in a $CO_2$ incubator at 37° C. The cells were separated with PBS containing 1 mM EDTA (Thermo Fisher Scientific, 15575-020), added to a round bottom 96-well plate (IWAKI) in a number of $1\times10^5$ per well, and centrifuged (500×g, 5 minutes, room temperature), then the supernatant was removed, 100 μL of a mogamulizumab solution was added to the cells (final concentration was 0 μg/mL, 1 μg/mL, 10 μg/mL, 100 μg/mL, or 1,000 μg/mL) to suspend them, and the suspension was incubated at room temperature for 1 hour. The suspension was centrifuged (500×g, 5 minutes, room temperature), then the supernatant was removed, and the cells were washed 3 times with 300 μL of PBS (500×g, 5 minutes, room temperature). Then, an antibody solution for staining (BV421-labeled anti-human CD56 antibody, PerCP/C5.5-labeled anti-human CD3 antibody, PE-Cy7-labeled anti-human CD16 antibody, or PE-labeled anti-human IgG Fc antibody (SouthernBiotech, 2043-09)) was added to suspend the cells, and the reaction was allowed at 4° C. for 30 minutes. The suspension was centrifuged (500×g, 5 minutes, room temperature), then the supernatant was removed, 100 μL of PBS was added to suspend the cells, measurement was performed by using a flow cytometer (BD LSRFortessa, BD Biosciences), and the results were analyzed by using the FlowJo software.

The results are shown in FIG. 7. It could be confirmed that mogamulizumab had bound to the NK cells. Under the high mogamulizumab concentration conditions, mogamulizumab could be bound to the cells of not only the population (i), but also the population (ii).

The invention claimed is:

1. A population of NK cells having the following characteristics (1), (2), and (3):
    (1) the NK cell is CD16-positive, highly expresses CD56, and is CD57-negative;
    (2) the NK cell is NKG2C-positive, is NKG2A-negative or lowly expresses NKG2A, and is CD94-positive; and
    (3) when the NK cell is used as effector cells (E), and co-cultured with K562 cells as target cells (T) at a mixing ratio (E:T) of 1:1, the NK cells show a cytotoxicity of 50% or higher.

2. The population according to claim 1, which contains a population of NK cells that highly express CD16, and a population of NK cells that lowly express CD16.

3. The population according to claim 1, wherein the NK cell highly expresses CD16.

4. The population according to claim 1, wherein the NK cell lowly expresses CD16.

5. A method for preparing the population according to claim 1, which comprises the following steps:
    collecting peripheral blood monocytes from a healthy volunteer using Ficoll;
    adding CD3 beads to the obtained peripheral blood monocytes, and incubating the monocytes and the beads at 4° C. for 15 minutes;
    adding a separation buffer to the monocytes and the beads to obtain a suspension, and centrifuging the suspension at 300×g for 10 minutes;
    removing a supernatant from the centrifuged suspension to obtain a residue, suspending the residue in a separation buffer, and adding the resulting suspension to LD Column wetted beforehand with the separation buffer;
    collecting an eluate from the LD Column, and centrifuging the eluate at 500×g for 5 minutes;
    removing a supernatant from the centrifuged eluate to obtain resultant cells, and suspending the resultant cells in NK medium I at a density of $5\times10^5$ cells/mL which are collected as primary NK cells;
    culturing the primary NK cells in a medium in a $CO_2$ incubator at 37° C. under 5% $CO_2$ atmosphere;
    collecting the cells on day 14 of the culturing step as the population; and
    wherein the medium is COSMEDIUM 008 containing 5% of human AB type serum which is obtained by inactivation at 56° C. for 30 minutes.

6. The method according to claim 5, wherein the population of primary NK cells has undergone the step of removing CD3-positive cells.

7. A pharmaceutical composition containing the population of NK cells according to claim 1, and an additive acceptable for a drug.

8. A pharmaceutical composition containing a population of NK cells, and a therapeutically effective amount of antibodies,
    wherein the population of NK cells is the population of NK cells according to claim 1.

9. The population according to claim 1, wherein the population is obtained from the following steps:
    collecting peripheral blood monocytes from a healthy volunteer using Ficoll;
    adding CD3 beads to the obtained peripheral blood monocytes, and incubating the monocytes and beads at 4° C. for 15 minutes;
    adding a separation buffer to the monocytes and the beads to obtain a suspension, and centrifuging the suspension at 300×g for 10 minutes;
    removing a supernatant from the centrifuged suspension to obtain a residue, suspending the residue in a separation buffer, and adding the resulting suspension to LD Column wetted beforehand with the separation buffer;
    collecting an eluate from the LD Column, and centrifuging the eluate at 500×g for 5 minutes;
    removing a supernatant from the centrifuged eluate to obtain resultant cells, and suspending the resultant cells in NK medium I at a density of $5\times10^5$ cells/mL which are collected as primary NK cells, and
    culturing the primary NK cells in a $CO_2$ incubator at 37° C. under 5% $CO_2$ atmosphere;
    collecting the cells on day 14 of the culturing step as the population; and
    wherein the NK medium I is COSMEDIUM 008 containing 5% of human AB type serum which is obtained by inactivation at 56° C. for 30 minutes.

10. A pharmaceutical composition containing a population of NK cells, and a therapeutically effective amount of antibodies bound thereto, in the absence of target cells.

11. The pharmaceutical composition according to claim 10, wherein the antibodies can induce antibody-dependent cellular cytotoxicity (ADCC).

12. The pharmaceutical composition according to claim 10, wherein at least a part of the antibodies bind with the NK cells.

* * * * *